United States Patent [19]

Junge et al.

[11] 4,179,500
[45] Dec. 18, 1979

[54] 1,4-DIHYDROPYRIDINE-SUGAR DERIVATIVES, AND THEIR USE AS MEDICAMENTS

[75] Inventors: Bodo Junge; Friedrich Bossert; Horst Meyer, all of Wuppertal; Egbert Wehinger, Velbert; Wulf Vater, Leverkusen; Arend Heise, Wuppertal; Stanislav Kazda, Wuppertal; Kurt Stoepel, Wuppertal, all of Fed. Rep. of Germany

[73] Assignee: Bayer Aktiengesellschaft, Leverkusen, Fed. Rep. of Germany

[21] Appl. No.: 828,135

[22] Filed: Aug. 26, 1977

[30] Foreign Application Priority Data

Sep. 16, 1976 [DE] Fed. Rep. of Germany ....... 2641746

[51] Int. Cl.$^2$ .................... A61K 31/70; A61K 31/72; C07H 15/00
[52] U.S. Cl. ........................................ 424/180; 536/1; 536/4; 536/18; 536/115; 536/116
[58] Field of Search ................. 536/4, 23, 115, 116, 536/119, 18; 424/180

[56] References Cited

U.S. PATENT DOCUMENTS

| | | | |
|---|---|---|---|
| 3,016,372 | 1/1962 | Krimmel | 536/4 |
| 3,950,324 | 4/1976 | Gey et al. | 536/4 |

*Primary Examiner*—Johnnie R. Brown
*Attorney, Agent, or Firm*—Sprung, Felfe, Horn, Lynch & Kramer

[57] ABSTRACT

The invention concerns the provision of novel 1,4-dihydropyridine-sugar derivatives and processes for their preparation. The invention also concerns pharmaceutical compositions containing the compounds of the invention and methods for their use. The products of the invention, such as 2-[1,4-dihydro-5-(2-propyl)-oxycarbonyl-2,6-dimethyl-4-m-nitrophenyl-3-pyridylcarbonyloxy]-ethyl β-D-glucopyranoside, are effective for the treatment of circulatory disorders and can be used as antihypertensive agents, vasodilators or coronary therapeutic agents.

13 Claims, 5 Drawing Figures

1,4-DIHYDROPYRIDINE-SUGAR DERIVATIVES, AND THEIR USE AS MEDICAMENTS

The present invention relates to 1,4-dihydropyridine-sugar derivatives, several processes for their preparation and their use as medicaments, in particular as agents which influence the circulatory system.

It has already been disclosed that 2,6-dimethyl-4-phenyl-1,4-dihydropyridine-3,5-dicarboxylic acid diethyl ester is obtained when benzaldehyde is reacted with β-amino-crotonic acid ethyl ester and acetoacetic acid ethyl ester (literature source: Fox, Lewis and Wenner, J. Org. Chem. 16, 1259 (1951)).

Furthermore, it is known that certain 1,4-dihydropyridines have interesting pharmacological properties (F. Bossert and W. Vater, Die Naturwissenschaften 58, 578 (1971)).

According to the present invention, we provide 1,4-dihydropyridine-sugar derivatives of the formula I in which
R represents an aryl radical which optionally contains 1 to 3 identical or different substituents selected from phenyl, alkyl, alkenyl, alkinyl, alkoxy, alkenoxy, alkinoxy, halogen, trifluoromethyl, trifluoromethoxy, hydroxyl, amino, alkylamino, nitro, cyano, azido, carbalkoxy, carboxamido, carboxyl, sulphonamido and $SO_m$-alkyl ($m=0, 1$ or $2$), or represents a thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl radical, the heterocyclic radicals mentioned optionally containing 1 to 3 identical or different substituents chosen from alkyl, alkenyl, alkinyl, alkoxy, alkenoxy, alkinoxy, halogen, trifluoromethyl, nitro, cyano, azido, hydroxyl, amino, alkylamino, carbalkoxy, carboxamido, carboxyl, sulphonamido and $SO_m$-alkyl ($m=0, 1$ or $2$), $R_1$ represents the radical $-S(O)_m R_6$, ($m=0, 1$ or $2$) or wherein,
$R_6$ represents a straight-chain, branched or cyclic saturated or unsaturated aliphatic hydrocarbon radical which is optionally interrupted in the chain by 1 or 2 oxygen atoms, or in which a hydrogen atom can be replaced by a hydroxyl group or by a phenoxy or phenyl group which is optionally substituted by halogen, cyano, amino, alkylamino, alkoxy, alkyl, trifluoromethyl or nitro or by an α-pyridyl, β- or γ-pyridyl group or by an amino group, this amino group optionally carrying either hydrogen and one substituent or two identical or different substituents from alkyl, alkoxyalkyl, aryl and aralkyl and these substituents optionally forming, with the nitrogen atom, a 5-membered to 7-membered ring which can contain an oxygen or sulphur atom as a further hetero-atom, or represents an aryl radical which optionally contains 1 to 3 identical or different substituents from the group alkyl, alkoxy, halogen, cyano, trifluoromethyl, trifluoromethoxy, amino, alkylamino or nitro, $R_2$ and $R_4$ are identical or different and represent hydrogen, a straight-chain or branched alkyl radical, an aryl radical or an aralkyl radical, $R_3$ denotes hydrogen or a straight-chain or branched alkyl radical which is optionally interrupted in the alkyl chain by one or two oxygen atoms, or represents an aryl or aralkyl radical and

$R_5$ represents a sugar residue [monosaccharide or oligosaccharide residue] or a sugar residue provided with protective groups or represents the group —O—X—Z in which
Z is a sugar residue [monosaccharide or oligosaccharide residue] or a sugar residue provided with protective groups and X represents an alkylene chain of 2 to 6 carbon atoms which is optionally interrupted by 1 or 2 oxygen atoms and in which one or more hydrogen atoms are optionally replaced by lower alkyl radicals or doubly bonded oxygen atoms.

Furthermore, it has been found that the new 1,4-dihydropyridine-sugar derivatives of the formula I are obtained when

(A) enamino compounds of the formula II are reacted with aldehydes of the formula III and β-carbonyl compounds of the formula IV wherein
R, $R_1$, $R_2$, $R_3$, and $R_4$ and $R_5$ have the meaning given above, in water or inert organic solvents and, if appropriate, protective groups in the sugar residues are then split off, or (B) enamino compounds of the formula V are reacted with aldehydes of the formula III $$R-CHO \qquad \text{III}$$

and carbonyl compounds of the formula VI $$R_1-CH_2-CO-R_2 \qquad \text{VI}$$

wherein
  R, $R_1$, $R_2$, $R_3$, $R_4$ and $R_5$ have the meaning given under process variant (A),
and, is appropriate, protective groups in the sugar residues are then removed, or
  (C) ylidene compounds of the formula VII $$R-CH=C\begin{smallmatrix}CO-R_2\\R_1\end{smallmatrix} \qquad \text{VII}$$

are reacted with amines of the formula VIII $$R_3-NH_2 \qquad \text{VIII}$$

and β-carbonyl compounds of the formula IV $$R_4-\underset{\underset{O}{\|}}{C}-CH_2-\underset{\underset{O}{\|}}{C}-R_5 \qquad \text{IV}$$

wherein
  R, $R_1$, $R_2$, $R_3$, $R_4$ and $R_5$ have the meaning given under (A),
and, if appropriate, protective groups in the sugar residues are then removed, or
  (D) ylidene compounds of the formula IX $$R-CH=C\begin{smallmatrix}CO-R_5\\COR_4\end{smallmatrix} \qquad \text{IX}$$

are reacted with amines of the formula VIII $$R_3-NH_2 \qquad \text{VIII}$$

and carbonyl compounds of the formula VI $$R_1-CH_2-\underset{\underset{O}{\|}}{C}-R_2 \qquad \text{VI}$$

wherein
  R, $R_1$, $R_2$, $R_3$, $R_4$ and $R_5$ have the meaning given under (A),
and, if appropriate, protective groups in the sugar residues are then removed, or
  (E) ylidene compounds of the formula VII $$R-CH=C\begin{smallmatrix}COR_2\\R_1\end{smallmatrix} \qquad \text{VII}$$

are reacted with enamino compounds of the formula V $$\begin{smallmatrix}R_4\\R_3-NH\end{smallmatrix}C=CH-CO-R_5 \qquad \text{V}$$

and, if appropriate, protective groups in the sugar residues are then removed, or
  (F) ylidene compounds of the formula IX $$R-CH=C\begin{smallmatrix}CO-R_5\\COR_4\end{smallmatrix} \qquad \text{IX}$$

are reacted with enamino compounds of the formula II $$\begin{smallmatrix}R_2\\R_3-NH\end{smallmatrix}C=CH-R_1 \qquad \text{II}$$

and, if appropriate, protective groups in the sugar residues are then removed.

The new 1,4-dihydropyridine derivatives according to the invention possess valuable pharmacological properties. Because of their influencing action on the circulatory system they can be used as anti-hypertensive agents, as vasodilators and as coronary therapeutic agents.

Depending on the nature of the starting materials used, the synthesis of the compounds according to the invention can be represented by the following equations, 2-(1,4-dihydro-5-methoxycarbonyl-2,6-dimethyl-4-o-nitrophenyl-3-pyridylcarbonyloxy)-ethyl β-D-gluocopyranoside and 3-O(1,4-dihydro-5-methoxycarbonyl-2,6-dimethyl-4-m-nitrophenyl-3-pyridylcarbonyl)-D-glucose being chosen as examples.

(A)

-continued

(B)

(C)

-continued

(D)

(E)

(F)

The formulae II, III, IV, V, VI, VII, VIII and IX provide a general definition of the starting materials. In these formulae R preferably represents a phenyl or naphthyl radical, in particular a phenyl radical, which optionally carries 1 or 2 identical or different substituents, substituents which may be mentioned being, preferably, phenyl, straight-chain or branched alkyl with 1 to 8, in particular 1 to 4, carbon atoms, cycloalkyl with 3 to 7, preferably 5 to 7, carbon atoms, alkenyl or alkinyl with 2 to 6 carbon atoms, in particular 2 to 3 carbon atoms, alkoxy with preferably 1 to 4, in particular 1 to 2, carbon atoms, alkenoxy and alkinoxy with 2 to 6, in particular 3 to 5, carbon atoms, halogen, such as fluorine, chlorine, bromine or iodine, especially fluorine, chlorine or bromine, trifluoromethyl, trifluoromethoxy, nitro, cyano, azido, hydroxyl, amino, monoalkylamino and dialkylamino with preferably 1 to 4, in particular 1 or 2, carbon atoms per alkyl group, carbalkoxy with preferably 2 to 4, in particular 2 or 3, carbon atoms, carboxamido carboxyl, sulphonamido or $SO_m$-alkyl, wherein m denotes 0 or 2 and alkyl preferably contains 1 to 4, in particular 1 or 2, carbon atoms, or represents a thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl radical. The heterocyclic radicals mentioned optionally carry 1 to 3 identical or different substituents, substituents which may be mentioned being, preferably, phenyl, straight-chain or branched alkyl with 1 to 8, in particular 1 to 4, carbon atoms, cycloalkyl with 3 to 7, preferably 5 to 7, carbon atoms, alkenyl or alkinyl with 2 to 6 carbon atoms, in particular 2 to 3 carbon atoms, alkoxy with preferably 1 to 4, in particular 1 to 2, carbon atoms, alkenoxy and alkinoxy with 2 to 6, in particular 3 to 5, carbon atoms, halogen such as fluorine, chlorine, bromine or iodine, in particular fluorine, chlorine or bromine, trifluoromethyl, nitro, cyano, azido, hydroxyl, amino, monoalkylamino and dialkylamino with preferably 1 to 4, in particular 1 or 2, carbon atoms per alkyl group, carbalkoxy with preferably 2 to 4, in particular 2 or 3, carbon atoms, carboxamido, carboxyl, sulphonamido or $SO_m$-alkyl, wherein m denotes 0 or 2 and alkyl preferably contains 1 to 4, in particular 1 or 2, carbon atoms. $R_1$ preferably represents the radicals $$-\underset{\underset{O}{\|}}{C}-R_6, \quad -\underset{\underset{O}{\|}}{C}-OR_6,$$

or $-S(O)_m-R_6$ ($m=0$, 1 or 2) or represents $$-\underset{\underset{O}{\|}}{C}-OR_5,$$

wherein $R_6$ represents a straight-chain, branched or cyclic saturated or unsaturated aliphatic hydrocarbon radical which is optionally interrupted in the chain by an oxygen atom or in which a hydrogen atom can be replaced by a hydroxyl group or by a phenoxy or phenyl group which is optionally substituted by halogen, such as fluorine, chlorine or bromine, cyano, amino, monoalkylamino and dialkylamino with 1 to 2 carbon atoms per alkyl group in each case, alkoxy with 1 to 4 carbon atoms, alkyl with 1 to 4 carbon atoms, trifluoromethyl or nitro, or by an α-pyridyl, β-pyridyl or γ-pyridyl group or by an amino group, this amino group optionally carrying either hydrogen and one substituent or two identical or different substituents from the group alkyl with up to 4 carbon atoms, alkoxyalkyl with up to 4 carbon atoms, phenyl and aralkyl, in particular benzyl or phenethyl, and these substituents optionally forming, with the nitrogen atom, a 5-membered to 7-membered ring which can contain an oxygen or sulphur atom as a further heteroatom, or represents an aryl radical, in particular a phenyl radical which can optionally carry 1 to 3 identical or different substituents, substituents which may be mentioned being straight-chain or branched alkyl with 1 to 4 carbon atoms, alkoxy with 1 to 2 carbon atoms, halogen, such as fluorine, chlorine or bromine, cyano, trifluoromethyl, trifluoromethoxy, amino, monoalkylamino and dialkylamino with 1 to 2 carbon atoms per alkyl group in each case or nitro, $R_2$ and $R_4$ preferably represent hydrogen, a straight-chain or branched alkyl radical with 1 to 4, in particular 1 to 2, carbon atoms, a phenyl radical or an aralkyl radical, in particular a benzyl or phenethyl radical, $R_3$ preferably represents a hydrogen atom or represents a straight-chain or branched alkyl radical with 1 to 8 carbon atoms, in particular 1 to 4 carbon atoms, the alkyl radical optionally being interrupted in the alkyl chain by an oxygen atom, or represents a phenyl radical or an aralkyl radical, in particular a benzyl or phenethyl radical and $R_5$ preferably represents a hexose, pentose or disaccharide residue, which are optionally in the form of derivatives formed with acyl, alkyl, acetal or ketal protective groups, or represents the group —O—X—Z, in which

Z is preferably a hexose (such as glucose, mannose, fructose, galactose), pentose (such as arabinose, xylose, rhammose) or disaccharide (such as sucrose, maltose) residue or a corresponding sugar residue in the form of a derivative formed with acyl, alkyl, acetal or ketal protective groups and

X preferably represents a short linear or branched, saturated carbon chain having up to carbon atoms, in particular the group —CH₂—CH₂—.

The compounds of the formula IV used as starting materials are not yet known but can be prepared by processes, known from the literature, for the preparation of β-keto acid esters (compare, for example, Houben-Weyl, Methoden der organischen Chemie (Methods of Organic Chemistry) VIII/4, 230 et seq. (1968)).

For illustration, the reaction of suitable sugar derivatives with dieketene, the splitting of acyl-acetoacetic esters and acyl-malonic esters and the ester condensation may be mentioned as an example of the preparative process:

If R₄ in the compounds of the formula IV is methyl, the reaction of suitable sugar derivatives with diketene is particularly preferred as the preparation process. This may be shown by two particular examples:

The reaction with diketene is preferably carried out without a solvent at temperatures between 80° and 140° C. and under normal pressure.

The enamino compounds of the formula V are also new. They can be prepared by splitting off water from β-keto esters of the formula IV and primary amines by paths known from the literature: (compare A. C. Cope, J. Amer. Chem. Soc. 67, 1017 (1945)).

The ylidene compounds of the formula IX are also new and are accessible, by paths known from the literature, by splitting off water from the β-keto esters of the formula IV and the adehydes of the formula III: (compare Org. Reactions XV, 204 et seq. (1967)).

The enamino compounds of the formula II used as starting materials are already known from the literature or can be prepared by methods known from the literature (compare A. C. Cope, J. Amer. Chem. Soc. 67, 1017 (1945)) and N. Gurswany et al., Indian, J. Chem. 11, 882 (1973)).

Examples which may be mentioned are: 4-amino-3-penten-2-one, 3-amino-1,3-diphenyl-acrolein, β-aminocrotonic acid cyclobutyl ester, β-aminocrotonic acid cyclopentyl ester, β-aminocrotonic acid cyclohexyl ester, β-aminocrotonic acid cyclopropylmethyl ester, β-aminocrotonic acid cyclophexenyl ester, β-aminocrotonic acid phenyl ester, β-aminocrotonic acid allyl ester, β-aminocrotonic acid methallyl ester, β-aminocrotonic acid butenyl ester, β-aminocrotonic acid propargyl ester, β-aminocrotonic acid butinyl ester, β-aminocrotonic acid 2-methoxyethyl ester, β-aminocrotonic acid 2-propoxyethyl ester, β-aminocrotonic acid 2-butoxyethyl ester, β-aminocrotonic acid 2-hydroxyethyl ester, β-aminocrotonic acid benzyl ester, β-aminocrotonic acid 2-phenylethyl ester, β-aminocrotonic acid 2-phenoxyethyl ester, β-aminocrotonic acid 4-chlorobenzyl ester, β-aminocrotonic acid 4-methylbenzyl ester, β-aminocrotonic acid 4-methoxybenzyl ester, β-aminocrotonic acid 4-nitrobenzyl ester, β-aminocrotonic acid 4-cyanobenzyl ester, β-aminocrotonic acid 4-dimethylaminobenzyl ester, β-aminocrotonic acid 3,4-dichlorobenzyl ester, β-aminocrotonic acid 2,4-dichlorobenzyl ester, β-aminocrotonic acid 3-chloro-4-trifluoromethylbenzyl ester, β-aminocrotonic acid 4-chloro-3-trifluoromethylbenzyl ester, β-aminocrotonic acid pyridyl-2-methyl ester, β-aminocrotonic acid 2-(N-benzyl-N-methylamino)ethyl ester, β-amino-β-phenylacrylic acid benzyl ester, β-amino-β-benzylacrylic acid allyl ester, 2-amino-1-methylsulphonyl-prop-1-ene, 2-amino-1-methylsulphonyl-but-1-ene, α-amino-β-methylsulphonylstyrene, 2-amino-1-ethylsulphonyl-but-1-ene, 2-amino-1-isobutylsulphonyl-prop-1-ene, 2-amino-1-cyclopentylsulphonyl-prop-1-ene, 2-amino-1-2-methoxyethylsulphonyl-prop-1-ene, 2-amino-1-2-propoxyethylsulphonyl-prop-1-ene, 2-amino-1-benzylsulphonyl-prop-1-ene, 2-amino-1-2-phenoxyethylsulphonyl-prop-1-ene, 2-amino-1-2-dimethylaminoethylsulphonyl-prop-1-ene, 2-amino-1-2-N-benzyl-N-methylaminoethylsulphonyl-prop-1-ene, 2-methylamino-1-methylsulphonyl-prop-1-ene, 2-methylamino-1-ethylsulphonyl-prop-1-ene, 2-ethylamino-1-benzylsulphonyl-prop-1-ene, 2-amino-1-phenylsulphonyl-prop-1-ene, 2-amino-1-4-chlorophenylsulphonyl-prop-1-ene, 2-amino-1-4-methylphenylsulphonyl-prop-1-ene, 2-amino-1-4-methoxyphenylsulphonyl-prop-1-ene, 2-amino-1-4-trifluoromethylphenylsulphonyl-prop-1-ene, 2-amino-1-4-nitrophenylsulphonyl-prop-1-ene, 2-amino-1-4-trifluoromethoxyphenylsulphonyl-prop-1-ene, 2-amino-1-3,4-dichlorophenylsulphonyl-prop-1-ene and 2-amino-1-4-chloro-3-trifluoromethylphenylsulphonyl-prop-1-ene.

The aldehydes of the formula III, employed as starting materials are already known or can be prepared by known methods (compare, for example, E. Mosettig, Org. Reactions VIII, 218 et seq. (1954)).

Examples which may be mentioned are: benzaldehyde, 2-, 3- or 4-phenylbenzaldehyde, α- or β-naphthylaldehyde, 2-, 3- or 4-methylbenzaldehyde, 2- or 4-n-butylbenzaldehyde, 2-, 3- or 4-isopropylbenzaldehyde, 2- or 4-cyclopropylbenzaldehyde, 2-vinylbenzaldehyde, 2-ethinylbenzaldehyde, 2-, 3- or 4-methoxybenzaldehyde, 2-cyclopropylmethoxybenzaldehyde, 2-propargyloxybenzaldehyde, 2-allyloxybenzaldehyde, 2-, 3- or 4-chloro/bromo/fluorobenzaldehyde, 2-, 3- or 4-trifluoromethylbenzaldehyde, 2-, 3- or 4-trifluoromethoxybenzaldehyde, 4-hydroxybenzaldehyde, 2-, 3- or 4-nitrobenzaldehyde, 2-, 3- or 4-cyanobenzaldehyde, 3-azidobenzaldehyde, 2-, 3- or 4-dimethylaminobenzaldehyde, 3-carbethoxybenzaldehyde, 3- or 4-carbamoylbenzaldehyde, 2-, 3- or 4-methylmercaptobenzaldehyde, 2-, 3- or 4-methylsulphinylbenzaldehyde, 2-, 3- or 4-methylsulphonylbenzaldehyde, 3,4,5-t methoxybenzaldehyde, 2,4- or 2,6-dichlorobenzaldehyde, 2,4-dimethylbenzaldehyde, 2,4- or 2,6-dinitrobenzaldehyde, 2-chloro-6-nitrobenzaldehyde, 4-chloro-2-nitrobenzaldehyde, 2-nitro-4-methoxybenzaldehyde, 2-nitro-4-cyanobenzaldehyde, 2-chloro-4-cyanobenzaldehyde, 4-cyano-2-methylbenzaldehyde, 3-methyl-4-trifluoromethylbenzaldehyde, 3-chloro-4-trifluoromethylbenzaldehyde, 4-chloro-3-sulphamoylbenzaldehyde, thiophene-2-aldehyde, furane-2-aldhyde, pyrrole-2-aldehyde, pyrazole-4-aldehyde, imidazole-2-aldehyde, oxazole-2-aldehyde, isoxazole-3-aldehyde, thiazole-2-aldehyde, pyridine-2-aldehyde, pyridine-3-aldehyde, pyridine-4-aldehyde, 4-methyl-pyridine-2-aldehyde, 6-methylpyridine-2-aldehyde, pyridazine-4-aldehyde, pyrimidine-4-aldehyde, pyrazine-2-aldehyde, quinoline-4-aldehyde, isoquinoline-1-aldehyde, indole-3-aldehyde, benzimidazole-2-aldehyde, quinazoline-2-aldehyde and quinoxaline-2-aldehyde.

The carbonyl compounds of the formula IV used as starting materials are already known from the literature or can be prepared by methods known from the literature (compare, for example, Houben-Weyl, Methoden der organischen Chemie (Methods of Organic Chemistry) VII/4, 230 et seq. (1968), and H. O. House and J. K. Larson, J. Org. Chem. 33, 61 (1968)).

Examples which may be mentioned are: acetylacetone, ω-benzoylacetophenone, formylacetic acid cyclopentyl ester, acetoacetic acid cyclopentyl ester, acetoacetic acid cyclopropylmethyl ester, acetoacetic acid cyclohexenyl ester, acetoacetic acid allyl ester, acetoacetic acid propargyl ester, acetoacetic acid 2-methoxyethyl ester, acetoacetic acid 2-butoxyethyl ester, acetoacetic acid benzyl ester, acetoacetic acid 2-phenylethyl ester, acetoacetic acid 2-phenoxyethyl ester, acetoacetic acid 4-chlorobenzyl ester, acetoacetic acid 3,4-dichlorobenzyl ester, acetoacetic acid 4-methoxybenzyl ester, acetoacetic acid 4-nitrobenzyl ester, acetoacetic acid 4-chloro-3-trifluoromethylphenyl ester, acetoacetic acid pyridyl-2-methyl ester, acetoacetic acid 2-(N-benzyl-N-methylamino)-ethyl ester, methylsulphonylacetone, n-butylsulphonylacetone, isobutylsulphonylacetone, cyclopentylsulphonylacetone, 2-methoxyethylsulphonylacetone, 2-propoxyethylsulphonylacetone, benzylsulphonylacetone, 4-chlorobenzylsulphonylacetone, 4-trifluoromethylbenzylsulphonylacetone, 2-phenylethylsulphonylacetone, 2-phenoxyethylsulphonylacetone, 2-dimethylaminoethylsulphonylacetone, 2-N-benzyl-N-methylaminoethylsulphonylacetone, 2-(piperidino-1)-ethylsulphonylacetone, phenylsulphonylacetone, 4-chlorophenylsulphonylacetone, 4-fluorophenylsulphonylacetone, 3,4-dichlorophenylsulphonylacetone, 4-trifluoromethylsulphonylacetone, 4-trifluoromethoxyphenylsulphonylacetone, 4-chloro-3-trifluoromethylphenylsulphonylacetone, 4-methylphenylsulphonylacetone, 4-tert.-butylphenylsulphonylacetone, 4-methoxyphenylsulphonylacetone, 4-nitrophenylsulphonylacetone, ω-methylsulphonylacetophenone.

The ylidene compounds of the formula VII used as starting materials are known from the literature or can be prepared by methods known from the literature (compare Org. Reactions XV, 204 et seq. (1967); and V. Baliah and C. Natarajan, Indian J. Chem. 8, 694, (1970)).

Examples which may be mentioned are: benzylideneacetylacetone, β,β-dibenzoylstyrene, 2'-nitrobenzylideneacetoacetic acid cyclobutyl ester, 3'-nitrobenzylideneacetoacetic acid cyclopentyl ester, 2'-trifluoromethylbenzylideneacetoacetic acid cyclohexyl ester, 2'-cyanobenzylideneacetoacetic acid cyclopropylmethyl ester, 2'-methoxybenzylidenecetoacetic acid cyclohexenyl ester, 2'-nitrobenzylideneacetoacetic acid allyl ester, 3'-nitrobenzylideneacetoacetic acid methylallyl ester, 3'-nitrobenzylideneacetoacetic acid propargyl ester, 2'-nitrobenzylideneacetoacetic acid 2-methoxyethyl ester, 2'-nitrobenzylideneacetoacetic acid 2-propoxyethyl ester, 3'-cyanobenzylideneacetoacetic acid 2-butoxyethyl ester, 2'-trifluoromethylbenzylideneacetoacetic acid benzyl ester, 3'-azidobenzylideneacetoacetic acid 2-phenylethyl ester, 3'-nitrobenzylideneacetoacetic acid 2-phenoxyethyl ester, 2'-nitrobenzylideneacetoacetic acid 4-chlorobenzyl ester, 2'-nitrobenzylideneacetoacetic acid 4-fluorobenzyl ester, 3'-nitrobenzylideneacetoacetic acid 4-methoxybenzyl ester, 2'-nitrobenzylideneacetoacetic acid 4-nitrobenzyl ester, 3'-nitrobenzylideneacetoacetic acid 4-dimethylaminobenzyl ester, 2'-nitrobenzylideneacetoacetic acid 3,4-dichlorobenzyl ester, 2'-nitrobenzylideneacetoacetic acid 4-chloro-3-trifluoromethylbenzyl ester, 2'-nitrobenzylidenebenzoylacetic acid allyl ester, 1-phenyl-2-methylsulphonyl-but-1-en-3-one, 1-2'-nitrophenyl-2-methylsulphonyl-but-1-en-3-one, 1-3'-nitrophenyl-2-ethylsulphonyl-but-1-en-3-one, 1-2'-trifluoromethylphenyl-2-methylsulphonyl-but-1-en-3-one, 1-2'-cyanophenyl-2-methylsulphonyl-but-1-en-3-one, 1-2'-methylphenyl-2-methylsulphonyl-but-1-en-3-one, 1-2'-methoxyphenyl-2-methylsulphonyl-but-1-en-3-one, 1-2'-chlorophenyl-2-methylsulphonyl-but-1-en-3-one, 1-3'-cyanophenyl-2-n-butylsulphonyl-but-1-en-3-one, 1-2'-nitrophenyl-2-(2-methoxyethylsulphonyl)-but-1-en-3-one, 1-3'-nitrophenyl-2-cyclopentylsulphonyl-but-1-en-3-one, 1-2'-trifluoromethylphenyl-2-(2-dimethylaminoethylsulphonyl)-but-1-en-3-one, 1-2'-cyanophenyl-2-2-(piperidino-1)-ethylsulphonyl-but-1-en-3-one, 1-2'-nitrophenyl-2-(N-benzyl-N-methylamino)-ethylsulphonyl-but-1-en-3-one, 1-3'nitrophenyl-2-benzylsulphonyl-but-1-en-3-one, 1-3'-nitrophenyl-2-2-(pyridyl-2)-ethylsulphonyl-but-1-en-3-one, 1-2'-trifluoromethylphenyl-2-phenylsulphonyl-but-1-en-3-one, 1-2'-nitrophenyl-2-(3-chlorophenylsulphonyl)-but-1-en-3-one, 1-3'-nitrophenyl-2-(4-methylphenylsulphonyl)-but-1-en-3-one, 1-3'-nitrophenyl-2-(4-methoxyphenylsulphonyl)-but-1-en-3-one, 1-2'-trifluoromethylphenyl-2-(4-nitrophenylsulphonyl)-but-1-en-3-one, 1-2'-nitrophenyl-2-(4-trifluoromethylphenylsulphonyl)-but-1-en-3-one, 1-2'-nitrophenyl-2-methylsulphonyl-pent-1-en-3-one, 1-3'-nitrophenyl-2-methylsulphonyl-4-phenyl-but-1-en-3-one and 1-2'-nitrophenyl-2-phenylsulphonyl-3-phenyl-prop-1-en-3-one.

The amines of the formula IV which can be used according to the invention are already known. Examples which may be mentioned are: ammonia, methylamine, n-propylamine, isopropylamine, n-butylamine, sec-butylamine, isobutylamine, β-methoxyethylamine, benzlamine and aniline.

Diluents which can be used for the preparation of the compounds according to the invention by process variants (A) to (F) are water and inert organic solvents. These include, preferably, alcohols, such as ethanol, methanol and isopropanol, ethers, such as dioxane, diethyl ether, tetrahydrofurane, glycol monomethyl ether and glycol dimethyl ether, or glacial acetic acid, dimethylformamide, dimethylsulphoxide, acetonitrile, pyridine and hexamethylphosphoric acid triamide.

The reaction temperatures can be varied within a fairly wide range. In general, the reaction is carried out between 20° C. and 150° C., preferably at the boiling point of the particular solvent.

The reaction can be carried out under normal pressure but also under increased pressure. In general, the reaction is carried out under normal pressure.

In general, in carrying out the process according to the invention the substances participating in the reaction are employed in about equimolar amounts.

In process variants (C) and (D), the amine of the formula VIII is preferably employed in excess.

Any protective groups which may be present in the sugar residues can be removed by processes which are in themselves known. For example, acyl protective groups are preferably removed by trans-esterification under basic conditions (for example with catalytic amounts of $NaOCH_3$ in methanol; Zemplen method) at room temperature and acetal or ketal protective groups are removed by hydrolysis in water/alcohol or water/dioxane mixtures under acid conditions at temperatures between 60° and 100° C. (compare, for example, Whistler and Wolfram, Methoden in Carbohydrate Chemistry (Methods in Carbohydrate Chemistry) II, page 215 et seq. and page 318 et seq).

The crude active compounds are preferably purified with the aid of chromatographic methods. In the case of compounds of the formula I with unprotected sugar residues, column chromatography on cellulose powder or on silica gel is preferred. Butanol or butanol/water mixtures or chloroform/ethanol mixtures are preferably used as the running agent.

The compounds according to the invention can occur in steroisomeric forms. The invention relates to both diastereomeric mixtures and uniform stereoisomers.

Depending on the number of the asymmetrical C atoms and the choice of the starting substances and procedures, the new compounds can be in the form of recemate mixtures, racemates or optical antipodes.

Racemate mixtures can be separated into the pure racemates in a known manner on the basis of the physicochemical differences of the constituents, for example by chromatography and/or fractional crystallisation.

Pure racemates can be resolved according to known methods, for example by recrystallisation from an optically active solvent, with the aid of micro-organisms or by reaction with an optically active acid or base which form salts with the racemic compound and separation of the salts obtained in this manner, for example on the basis of their different solubilities, into the diastereomers from which the antipodes can be liberated by the action of suitable agents. Particularly customary optically active acids are, for example, the d- and α-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end products in the form of the pure racemates or optical antipodes by employing starting substances, containing one or more asymmetrical C atoms, in the form of the pure racemates or optical antipodes.

1,4-Dihydropyridines of the formula I
in which
R represents a phenyl radical which optionally carries one or two substituents from the group nitro, halogen, trifluoromethyl or cyano, or represents a pyridyl, the following active compounds according to the invention may be mentioned: 2-(1,4-dihydro-5-methoxycarbonyl-2,6-dimethyl-4-m-nitrophenyl-3-pyridylcarbonyloxy)-ethyl β-glucopyranoside, 2-[1,4-dihydro-5-(1-propen-2-yl)-oxycarbonyl-2,6-dimethyl-4-o-cyanophenyl-3- pyridylcarbonyloxy]-ethyl β-D-glucopyranoside, 2-(1,4-dihydro-5-phenylsulphonyl-2,6-dimethyl-4-o-nitrophenyl-3-pyridylcarbonyloxy)-ethyl β-D-glucopyranoside, 2-(1,4-dihydro-5-ethylsulphonyl-2,6-dimethyl-4-o-nitrophenyl-3-pyridylcarbonyloxy)-ethyl β-D-glucopyranoside, 2-[1,4-dihydro-5-ethoxycarbonyl-2,6-dimethyl-4-(pyridyl-2)-3-pyridylcarbonyloxy]-ethyl β-glucopyranoside, 2-[1,4-dihydro-5-(2-propyl)-oxycarbonyl-2,6-dimethyl-4-o-nitrophenyl-3-pyridylcarbonyloxy]-ethyl β-D-galactopyranoside, 2-(1,4-dihydro-5-methoxycarbonyl-2,6-dimethyl-4-m-nitrophenyl-3-pyridylcarbonyloxy)-ethyl β-D-xylopyranoside, 2-(1,4-dihydro-5-methoxycarbonyl-2,6-dimethyl-4-o-nitrophenyl-3-pyridylcarbonyloxy)-ethyl β-D-ribofuranoside, 2-(1,4-dihydro-5-methoxycarbonyl-2,6-dimethyl-4-o-nitrophenyl-3-pyridylcarbonyloxy)-ethyl-[O-α-D-glucopyranosyl-(1→4)] β-D-glucopyranoside, 3-O-(1,4-dihydro-5-ethoxycarbonyl-2,6-dimethyl-4-o-nitrophenyl-3-pyridylcarbonyl)-D-glucose, 3-O-(1,4-dihydro-5-cyclopentyloxycarbonyl-2,6-dimethyl-4-o-nitrophenyl-3-pyridylcarbonyl)-D-glucose, 6-O-(1,4-dihydro-5-methoxycarbonyl-2,6-dimethyl-4-m-nitrophenyl-3-pyridylcarbonyl)-D-glucose, 6-O-(1,4-dihydro-5-methoxycarbonyl-2,6-dimethyl-4-o-nitrophenyl-3-pyridylcarbonyl)-D-glucose, 6-O-(1,4-dihydro-5-cyclopentyloxycarbonyl-2,6-dimethyl-4-o-nitrophenyl-3-pyridylcarbonyl)-D-glucose, 2-O-(1,4-dihydro-5-ethoxycarbonyl-2,6-dimethyl-4-m-nitrophenyl-3-pyridylcarbonyl)-D-glucose, 4-O-(1,4-dihydro-5-cyclopentyloxycarbonyl-2,6-dimethyl-4-o-nitrophenyl-3-pyridylcarbonyl)-D-glucose, 6-O-(1,4-dihydro-5-ethoxycarbonyl-2,6-dimethyl-4-m-nitrophenyl-3-pyridylcarbonyl)-D-galactose, 3-O-[1,4-dihydro-5-(2-propyl)-oxycarbonyl-2,6-dimethyl-4-o-nitrophenyl-3-pyridylcarbonyl]-D-fructose and 1-O-(1,4-dihydro-5-methoxycarbonyl-2,6-dimethyl-4-m-nitrophenyl-3-pyridylcarbonyl)-D-fructose.

The new compounds are substances which can be used as medicaments. They have a broad and diverse spectrum of pharmacological activity.

In detail, the following main actions can be demonstrated in animal experiments:

(1) The compounds produce a distinct and long-lasting dilation of the coronary vessels on parenteral, oral and perlingual administration.

This action on the coronary vessels is intensified by a simultaneous nitrite-like effect of reducing the load on the heart.

They influence or modify the heart metabolism in the sense of an energy saving.

(2) The excitability of the stimulus formation and excitation conduction system within the heart is lowered, so that an anti-fibrillation action which can be demonstrated at therapeutic doses results.

(3) The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).

(4) The compounds lower the blood pressure of normotonic and hypertonic animals and can thus be used as anti-hypertensive agents.

(5) The compounds have a strong muscular-spasmolytic action, which manifests itself on the smooth muscle of the stomach, the intestinal tract, the urogenital tract and the respiratory system.

Because of these properties, the compounds according to the invention are particularly suitable for the prophylaxis and therapy of acute and chronic ischemic heart disease in the broadest sense, for the therapy of hypertension and for the treatment of cerebral and peripheral circularoty disturbances.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules, and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with on or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide of mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate benzyl alcohol, benzyl benzoate, propulene glycol, 1,3-butylene glycol, dimethylfoimamide, oils [for example, ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 0.5 mg to 1.5 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including relief of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably orally or parenterally (especially intravenously) Preferred pharmaceutical compositions and medicaments are therefore those adapted for oral or parenteral administration.

In general, it has proved advantageous, in the case of intravenous administration, to administer amounts of about 0.01 to 15 mg/kg, preferably about 0.05 to 1 mg/kg, of body weight per day in order to achieve effective results; in the case of oral administration the dosage is about 0.05 to 10 mg/kg, preferably 0.1 to 5 mg/kg, of body weight per day.

Nevertheless, it can at times be necessary to deviate from the amounts mentioned, and in particular to do so as a function of the body weight of the test animal or the nature of the method of administration, but also because of the type of animal and its individual behaviour towards the medicament, or the nature of the formulation of the medicament and the time or interval at which it is administered. Thus it can in some cases suffice to manage with less than the above-mentioned minimum amount, whilst in other cases the upper limit mentioned must be exceeded. Where larger amounts are administered it can be advisable to divide these into several individual administrations over the course of the day.

Preparation Examples

EXAMPLE 1

2-[1,4-Dihydro-5-(2-propyl)-oxycarbonyl-2,6-dimethyl-4-m-nitrophenyl-3-pyridylcarbonyloxy]-ethyl β-D-glucopyranoside 2.4 g (5 mmols) of 2-acetonylcarbonyloxyethyl 2,3,4,6-tetra-O-acetyl-β-D-glucopyranoside, 0.75 g (5 mmols) of m-nitrobenzaldehyde and 0.72 g (5 mmols) of β-aminocrotonic acid isopropyl ester are heated to the boil in 10 ml of ethanol for 24 hours. The solvent is then removed on a rotary evaporator.

The residue is taken up in 100 ml of a 0.1% strength solution of sodium methanolate in methanol and kept for 12 hours at room temperature.

The solution is then diluted with 30 ml of water, neutralised with a weakly acid ion exchanger (H+ form), the ion exchanger is filtered off and the solution is brought to dryness on a rotary evaporator. The residue is dissolved in a little butanol, which is saturated with water, and the solution is discharged onto a column (length: 50 cm; φ: 2.5 cm) filled with cellulose (Avicel; Merck, Darmstadt).

Water-saturated n-butanol is used as the running agent. Fractions of, in each case, 200 drops are collected. The individual fractions are combined according to the result of a thin layer chromatography test on silica gel plates (running agent: CHCl₃/ethanol, 2:1).

Yield: 2.2 g (non-crystalline)

$C_{26}H_{34}N_2O_{12}$ (566.6). Calculated: C 55.1; H 6.05; N 4.9. Found: C 55.8; H 5.8; N 5.1.

EXAMPLES 2 to 7

The following compounds were prepared analogously to the compound of Example 1:

EXAMPLE 2:

2-(1,4-Dihydro-5-methoxycarbonyl-2,6-dimethyl-4-o-nitrophenyl-3-pyridylcarbonyloxy)-ethyl β-D-glucopyranoside $C_{24}H_{30}N_2O_{12}$ (538.5). Calculated: C 55.3; H 5.61; N 5.2. Found: C 53.3; H 5.6; N 5.1.

EXAMPLE 3

2-(1,4-Dihydro-5-cyclopentyloxycarbonyl-2,6-dimethyl-4-o-nitrophenyl-3-pyridylcarbonyloxy)-ethyl β-D-glucopyranoside $C_{28}H_{36}N_2O_{12}$ (592.6). Calculated: C 56.7; H 6.13; N 4.7. Found: C 56.7; H 6.5; N 4.2.

EXAMPLE 4

2-(1,4-Dihydro-5-n-butoxycarbonyl-2,6-dimethyl-4-m-nitrophenyl-3-pyridylcarbonyloxy)-ethyl β-D-glucopyranoside C$_{27}$H$_{36}$N$_2$O$_{12}$ (580.6). Calculated: C 55.9; H 6.3; N 4.8. Found: C 56.5; H 6.3; N 4.5.

EXAMPLE 5

2-(1,4-Dihydro-5-ethoxycarbonyl-2,6-dimethyl-4-o-trifluoromethylphenyl-3-pyridylcarbonyloxy)-ethyl β-D-glucopyranoside C$_{26}$H$_{32}$F$_3$NO$_{10}$ (575.6). Calculated: C 54.3; H 5.6; N 2.4. Found: C 53.9; H 5.8; N 2.1.

EXAMPLE 6

2-(1,4-Dihydro-5-methoxycarbonyl-2,6-dimethyl-4-o-chlorophenyl-3-pyridylcarbonyloxy)-ethyl β-D-glucopyranoside C$_{24}$H$_{32}$ClNO$_{10}$ (528.0). Calculated: C 54.6; H 5.7; N 2.7; Cl 6.7. Found: C 54.1; H 5.5; N 2.5; Cl 6.9.

EXAMPLE 7

2-(1,4-Dihydro-5-(2-propyl)-oxycarbonyl-2,6-dimethyl-4-o-chlorophenyl-3-pyridylcarbonyloxy)-ethyl β-D-glucopyranoside C$_{26}$H$_{34}$ClNO$_{10}$ (556.1). Calculated: C 56.2; H 6.2; N 2.5; Cl 6.4. Found: C 54.8; H 6.2; N 2.4; Cl 6.6.

Preparation of the starting compound

2-Acetonylcarbonyloxyethyl 2,3,4,6-tetra-O-acetyl β-D-glucopyranoside 0.5 ml of triethylamine is added to 23 g (59 mmoles) of 2-hydroxyethyl 2,3,4,6-tetra-O-acetyl β-D-glucopyranoside and the mixture is warmed to 80° C. 5 ml (65 mmols) of diketene are added dropwise to this mixture, with the exclusion of moisture and whilst stir- ring. The temperature rises up to 110° C. during this procedure. The mixture is warmed at 100° C. for a further hour and, after cooling, petroleum ether is added to the residue whereupon the reaction product crystallises out.

Yield: 25.5 g.

After recrystallisation from isopropanol, the compound melts at 78°–80° C.

EXAMPLE 8

1,2;5,6-Di-O-isopropylidene-3-O-(1,4-dihydro-5-methoxycarbonyl-2,6-dimethyl-4-m-nitrophenyl-3-pyridylcarbonyl)-α-D-glucofuranose.

4.8 g (13.9 mmols) of 3-O-acetonylcarbonyl-1,2: 5,6-di-O-isopropylidene-α-D-glucofuranose, 1.6 g (13.9 mmols) of β-aminocrotonic acid methyl ester and 2.1 g (13.9 mmols) of m-nitrobenzaldehyde are heated in 30 ml of ethanol for 24 hours under reflux.

The solvent is then removed in a rotary evaporator.

The crude product is purified by chromatography on a column filled with $Al_2O_3$. Chloroform is used as the running agent.

The individual fractions are tested by thin layer chromatography on silica gel plates (running agent: chloroform/ethyl acetate 2:1; Rf value: 0.5–0.6). Yield: 5.5 g.

The non-crystalline product is a mixture of two diastereomeric compounds. A partial separation of the diastereomers takes place on the $Al_2O_3$ column.

A better separation is achieved by Craig distribution.

Figure 1:
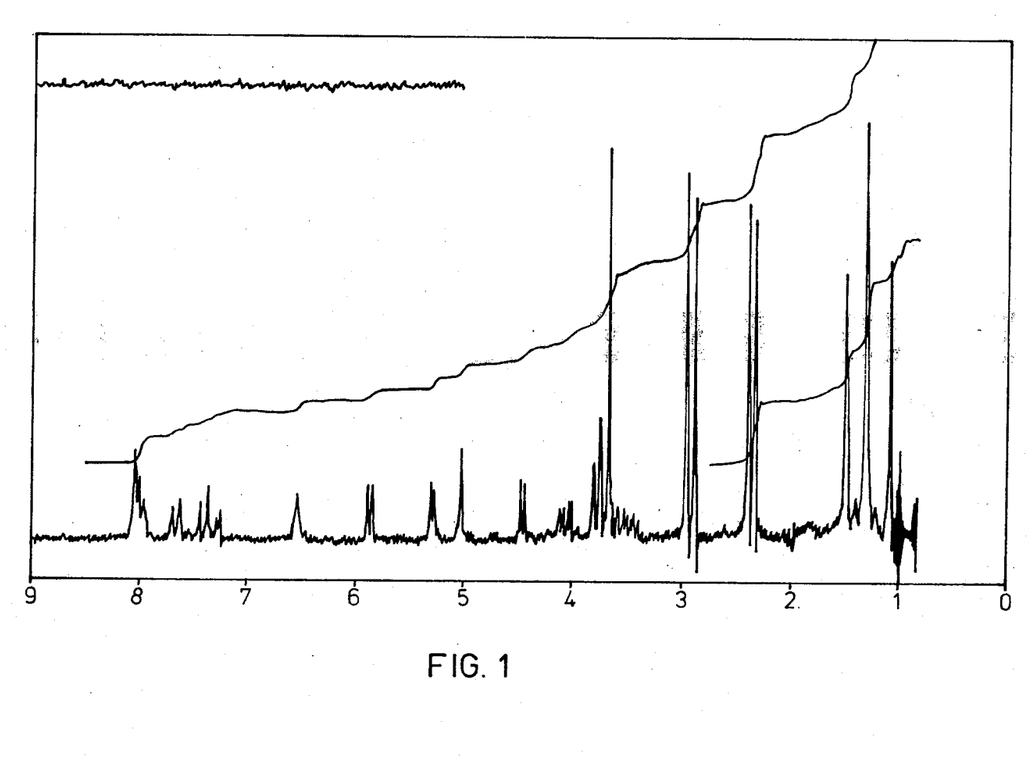
Figure 2:
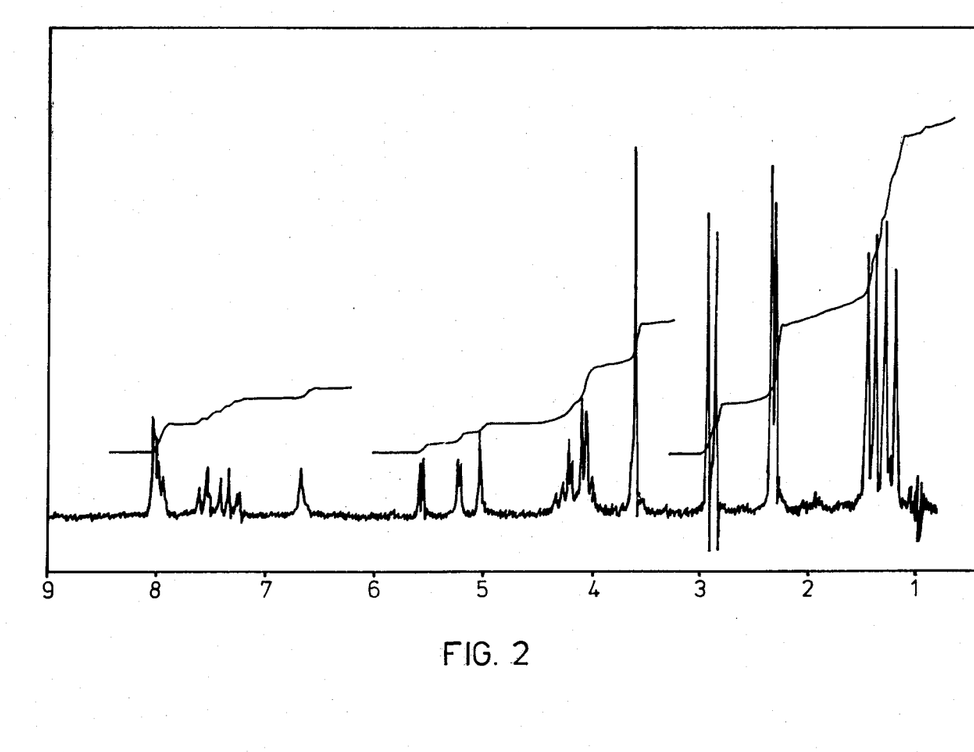

FIG. 1 and FIG. 2 show the proton resonance spectrum of both diastereomers measured at 100 MHz in deuterochloroform.

EXAMPLE 9

1,2-O-Isopropylidene-3-O-(1,4-dihydro-5-methoxycarbonyl-2,6-dimethyl-4-m-nitrophenyl-3-pyridylcarbonyl)-α-D-glucofuranose 5.5 g of the diasteremeric mixture from Example 9 are warmed to 60° C. in 35 ml of ethanol, 25 ml of $H_2O$ and 1 ml of concentrated sulphuric acid for 20 minutes. After cooling, the mixture is diluted with 40 ml of water. The precipitate which has separated out is filtered off, washed with water until neutral and taken up in chloroform. The chloroform solution is dried with $Na_2SO_4$ and brought to dryness in a rotary evaporator. The residue, dissolved in a little chloroform, is applied to a column (length: 25 cm; φ 2.5 cm) charged with neutral $Al_2O_3$. Elution is carried out first with chloroform, then with chloroform/ethanol 20:1 and finally with chloroform/ethanol 10:1.

The individual fractions are tested by thin layer chromatography on silica gel plates (running agent: $CHCl_3$/MeOH 10:1, Rf value: 0.4–0.5).

Yield: 3.5 g.

The non-crystalline product is a mixture of diastereoisomeric compounds. A partial separation of the diastereomers takes place on the $Al_2O_3$ column when the column is charged with only a very little substance and very small fractions are collected. Separation of the diastereomers is also effected by crystallisation from dioxane/water 1:1.

The diastereomer crystallising out of this solvent mixture has a solidification point of 220°–221° C.

Figure 3:
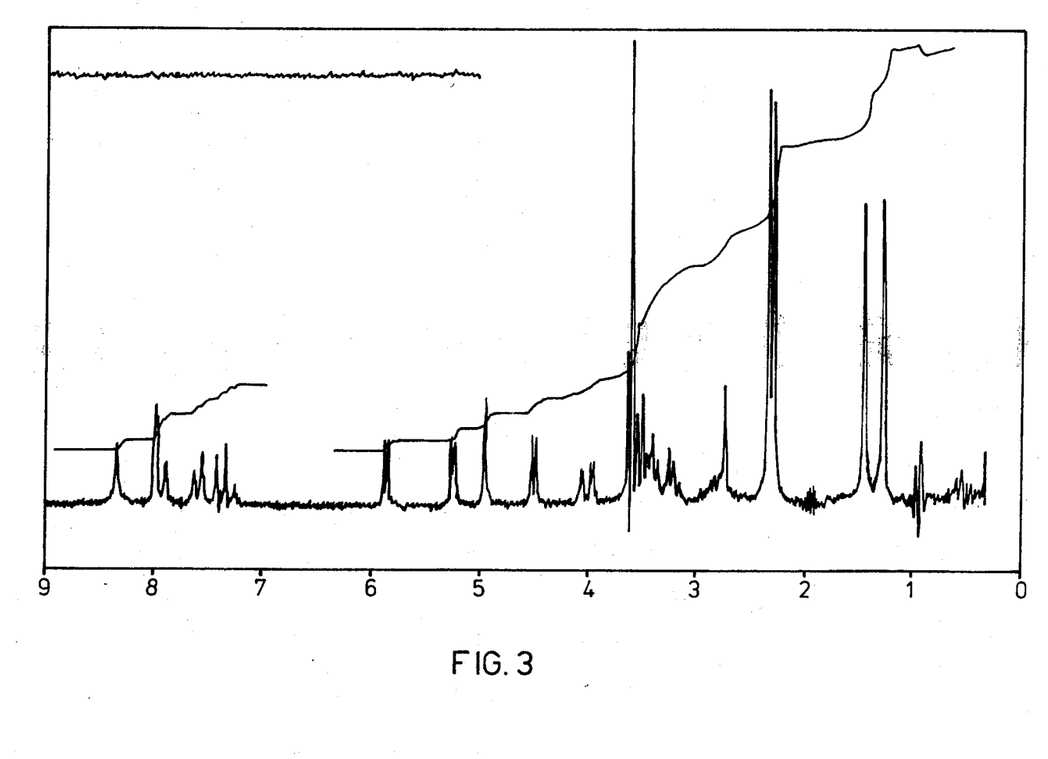
Figure 4:
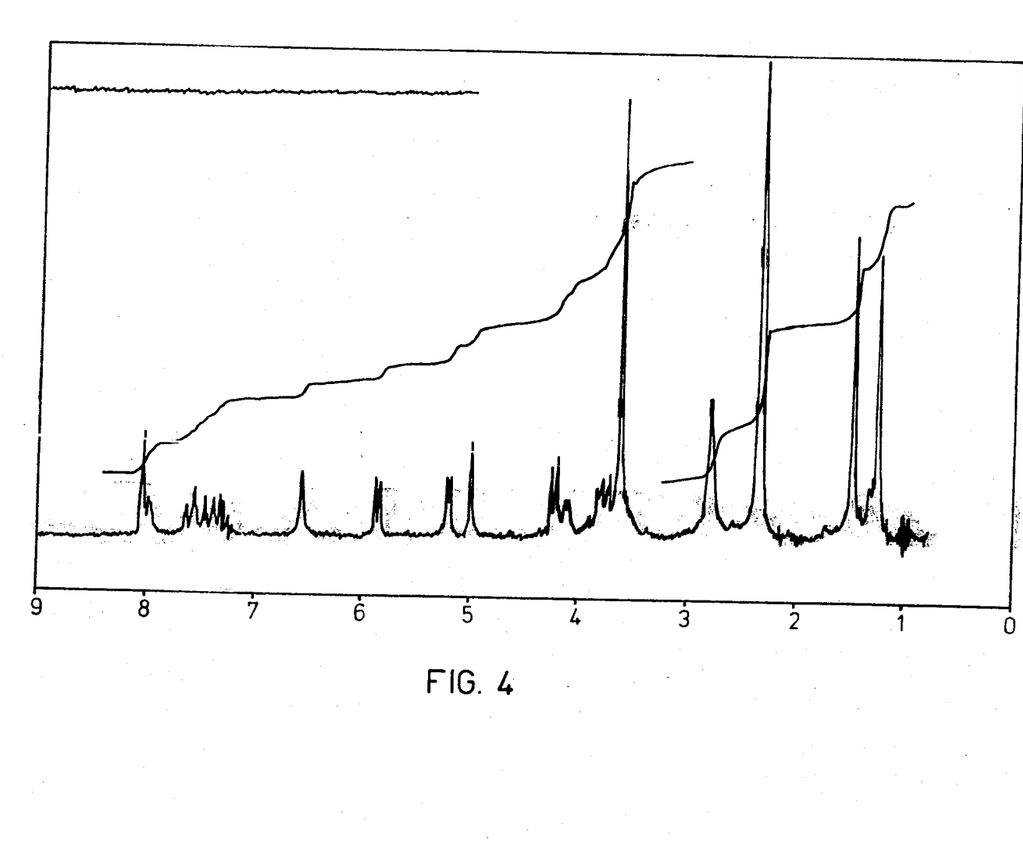

FIG. 3 shows the proton resonance spectrum of this compound, measured at 100 MHz in $CDCl_3$ dimethylsulphoxide (small quantity). FIG. 4 shows the proton resonance spectrum of the other diasereomer at 100 MHz in $CDCl_3$. It is obtained, according to the procedure of Example 9, from the diastereomer of Example 8 which is characterised in FIG. 2.

EXAMPLE 10

3-O-(1,4-Dihydro-5-methoxycarbonyl-2,6-dimethyl-4-m-nitrophenyl-3-pyridylcarbonyl)-D-glucose 2.8 g of the diastereomer mixture from Example 9 are warmed in 15 ml of 2 N $H_2SO_4$ and 15 ml of dioxane for 30 minutes under reflux.

The reaction mixture is diluted with water and neutralised with $BaCO_3$. The precipitate is filtered off and the filtrate is brought to dryness in a rotary evaporator. The residue is eluted, with $CHCl_3$/ethanol 5:1, on a column filled with silica gel 60 (Merck, Darmstadt). The individual fractions are tested by thin layer chromatography on silica gel plates (running agent: $CHCl_3$/MeOH 10:1 or $CHCL_3$/MeOH 3:1, Rf value: 0.1 or 0.6 respectively).

Yield: 1.1 g.

Figure 5:
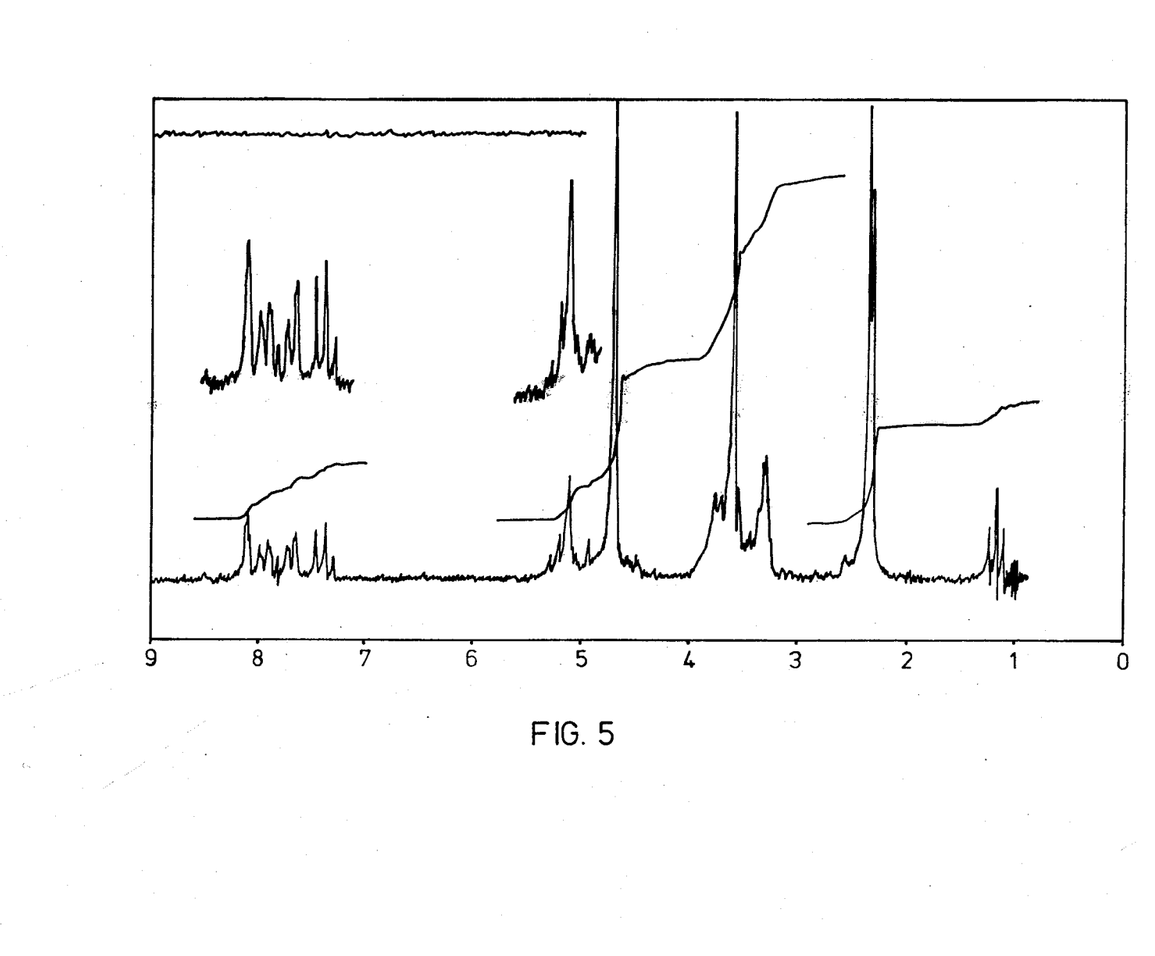

FIG. 5 shows the proton resonance spectrum of this product measured at 100 MHz in $CD_3OD$.

Preparation of the starting compound

3-O-Acetonylcarbonyl-1,2;5,6-di-O-isopropylidene-α-D-glucofuranose

1.2 ml of triethylamine are added to 39 g (150 mmols) of 1,2;5,6-di-O-isopropylidene-α-D-glucofuranose and the mixture is warmed to 100° C. 14.4 ml (175 mmols) of 94% strength diketene are added dropwise, whereupon the temperature rapidly rises to 130° C. The mixture is subsequently stirred for a further 15 minutes at 100° C. Petroleum ether is then added to the reaction mixture and the mixture is stirred thoroughly. The petroleum ether is decanted off and the purification operation is repeated several times. Finally, residual petroleum ether is removed in a rotary evaportor. Thin layer chromatography on silica gel plates with $CHCl_3/CH_3COOC_2H_5$ 2:1 as the running agent shows a uniform reaction product.

(Rf value: 0.63).

Yield: 49 g (non-crystalline).

What is claimed is:

1. A 1,4-Dihydropyridine-sugar derivative of the formula I in which

R represents a phenyl radical which is unsubstituted or carries one or two of the substituents nitro, halogen, trifluoromethyl and cyano, or represents pyridyl, quinolyl or isoquinolyl, the pyridyl radical being unsubstituted or substituted by alkyl with 1 to 4 carbon atoms, $R_1$ represents a group of the formula and $-S(O)_m-R_6$ ($m=0$ or 2), wherein $R_6$ denotes an alkyl, alkenyl, cycloalkyl or an alkoxyalkyl radical with up to 6 carbon atoms in each case or wherein $R_6$ represents benzyl, phenethyl, phenoxyethyl β-aminoethyl which carries a methyl and a benzyl group on the nitrogen, $R_2$ and $R_4$ identical or different and represent hydrogen, alkyl with 1 to 2 carbon atoms or benzyl, $R_3$ represents hydrogen, alkyl with 1 to 4 carbon atoms or benzyl and $R_5$ represents a D-glucose, D-fructose, D-mannose, D-galactose, D-ribose, 2-desoxy-D-ribose, D-xylose, D- and L-arabinose, maltose, lactose, saccharose, isomaltose and cellobiose radical, which is bonded to the carbonyl group of the 1,4-dihydropyridine radical either directly or via a short bridge —O—X—, wherein X represents an alkylene chain of 2 to 4 carbon atoms, the bond to the sugar being via the hydroxyl groups of the sugar unit and being both an ester bond and a glycosidic bond.

2. A compound according to claim 1 wherein $R_6$ is benzyl.

3. A compound of claim 1 wherein halogen, in each occurrence is chlorine, bromine or fluorine.

4. A compound according to claim 1 in the form of a diastereomeric mixture.

5. A compound according to claim 1, wherein $R_5$ represents one of said hexose, pentose or disaccharide residues, optionally in the form of a derivative with an acetyl, methyl, benzylidene or isopropylidene protective group, or represents the group —O—X—Z, in which Z is a hexose, pentose or disaccharide residue or a corresponding sugar residue in the form of a derivative with an acetyl, methyl, benzylidene or isopropylidene protective group and X represents a linear or branched alkylene or oxaalkylene chain having 2 to 6 carbon atoms and optionally interrupted by one or two oxygen atoms.

6. A pharmaceutical composition containing as an active ingredient an effective amount of a compound according to claim 1 in admixture with a solid or liquefied gaseous diluent or in admixture with a liquid diluent.

7. A pharmaceutical composition containing as an active ingredient an effective amount of a compound according to claim 1 in the form of a sterile or isotonic aqueous solution.

8. A composition according to claim 6 containing from 0.5 to 95% by weight of the said active ingredient.

9. A medicament in the form of a tablet, pill, dragee, capsule, ampoule, or suppository comprising a unit dose of a compound according to claim 1 as an active ingredient and an inert pharmaceutical carrier.

10. A medicament in dosage unit form comprising as an active ingredient a compound according to claim 1 together with an inert pharmaceutical carrier.

11. A method of combating circulatory disease influenced by vasodilation in a warm-blooded animal which comprises administering to said animal an effective amount of an active compound according to claim 1 either alone or in admixture with a diluent or in the form of a medicament.

12. A method according to claim 11 in which the active compound is administered in an amount of 0.01 to 15 mg per kg body weight per day.

13. A method according to claim 11 in which the active ingredient is administered orally or parenterally.

* * * * *